United States Patent [19]

Roncarolo

[11] Patent Number: 5,405,751
[45] Date of Patent: Apr. 11, 1995

[54] PRENATAL DIAGNOSIS BY CYTOKINE-INDUCED PROLIFERATION OF FETAL T-CELLS

[75] Inventor: Maria-Grazia Roncarolo, Los Altos, Calif.

[73] Assignee: Schering Corporation, Kenilworth, N.J.

[21] Appl. No.: 180,748

[22] Filed: Jan. 12, 1994

[51] Int. Cl.$^6$ .......................... C12Q 1/02; C12Q 1/68; G01N 33/53
[52] U.S. Cl. ..................................... 435/7.24; 435/4; 435/6; 435/29; 435/240.2; 436/63
[58] Field of Search ...................... 435/4, 6, 7.24, 29, 435/240, 2; 436/63

[56] References Cited

PUBLICATIONS

P. Hohlfeld et al, *Pediatr. Infect. Dis. Journ.*, 9, 878–881, 1990.

"Early Prenatal Diagnosis," *British Medical Journal*, 299:1211–1212, Nov. 11, 1989.

H. Brandenburg, et al., "Fetal Loss Rate After Chorionic Villus Sampling and Subsequent Ammiocentesis," *American Journal of Medical Genetics*, 35:178–180, 1990.

Stephen J. Carlan, et al., "Effect of maternal-fetal movement on concentration of cells obtained at genetic amniocentesis," *American Journal of Obstetrics and Gynecology*, 163:490–493, Aug. 1990.

Winston W. Chen, "Studies on the origin of human amniotic fluid cells by Immunofluorescent staining of keratin filaments,"0 *Journal of Medical Genetics*, 19:433–436, 1982.

S. K. F. Chong, et al., "Subarachnoid Cyst with Hydercephalus—A Complication of Mid-Trimester Amniocentesis," *Prenatal Diagnosis*, 9: 677–679, 1989.

Fernand Daffos, "Access to the Other Patient," *Seminars in Perinatology*, 13(4):252–259, Aug. 1989.

B. Rafael Elejalde, et al., "Prospective Study of Amniocentesis Performed Between Weeks 9 and 16 of Gestation: Its Feasibility, Risks, Complications and Use in Early Genetic Prenatal Diagnosis," *American Journal of Medical Genetics*, 35:188–196, 1990.

Mark I. Evans, et al., "Genetic diagnosis in the first trimester: The norm for the 1990s," *American Journal of Obstetrics and Gynecology*, 160:1332–1339, 1989.

W Furhmann, "Impact, logistics and prospects of traditional prenatal diagnosis," *Clinical Genetics*, 36:378–385, 1989.

Eliane Gluckman, et al., "Hematopoietic Reconstitution in a Patient With Fanconi's Anemia by means of Umbilical-cord Blood From an HLA-Identical Sibling," *The New England Journal of Medicine*, 1174–1178, Oct. 26, 1989.

Izumi Hayashi, et al., "Replacement of serum by homones permits growth of cells in defined medium," *Nature*, 259:132–134, Jan. 15, 1976.

Wolfgang Holzgreve, et al., "Genetic Aspects of Fetal Disease," *Seminars in Perinatology*, 13(4):260–277, Aug. 1989.

Helen M. Kingston, "Prenatal Diagnosis," *British Medical Journal*, 298(6684):1368–1371, May 20, 1989.

Tomas Leanderson, "Assays for Lymphokines Supporting B Cell Growth," *Immunological Methods*, 3:201–209, 1985.

David H, Ledbetter, et al., "Cytogenetic results of chorionic villus sampling: High success rate and diagnostic accuracy in the United States collaborative study,"

(List continued on next page.)

*Primary Examiner*—David Saunders
*Attorney, Agent, or Firm*—Edwin P. Ching; Karen B. Dow; Joe Liebeschuetz

[57] ABSTRACT

The invention provides improved methods of prenatal diagnosis that can be performed earlier in pregnancy, and/or with greater safety, and/or rapidity, and/or with greater accuracy than conventional methods. A volume of amniotic fluid containing fetal cells is extracted from a pregnant woman, and the fetal T-cells are propagated in a culture medium comprising one or more cytokines. The fetal T-cells are then diagnosed for genetic defects.

16 Claims, No Drawings

OTHER PUBLICATIONS

*American Journal of Obstetrics and Gynecology*, 162:495–501, Feb. 1990.

G. Mandon, et al., "15 Years of Prenatal Diagnosis of Inherited Metabolic Diseases: the Lyons Experience," *J. Inher. Metab. Dis.*, 12(2):257–259, 1989.

Giovanni Monni, et al., "Second–Trimester Placental Biopsy Versus Amniocentesis for Prenatal Diagnosis of β–Thalassemia,"*The New England Journal of Medicine*, 322(1):60–61, Jan. 4, 1990.

Hiroki Murakami, et al., "Growth of hybridoma cells in serum–free medium: Ethanolamine is an essential component,"*Proc. Natl. Acad. Sci. USA*, 79:1158–1162, Feb. 1982.

J. Nevin, et al., "Early Amniocentesis: Experience of 222 Consecutive Patients, 1989–1988," *Prenatal Diagnosis*, 10:79–83, 1990.

R. Nisani, et al., "The Dilemma of Chromosomal Mosaicism in Chorionic Villus Sampling—'Direct' Versus Long –Term Cultures," *Prenatal Diagnosis*, 9:223–226, 1989.

Lawrence D. Platt, et al., "Prenatal Diagnosis—When And How?" *the New England Journal Of Medicine*, 327(9):636–638, Aug. 27, 1992.

George G. Rhoads, et al., "The Safety and Efficacy of Chorionic Villus Sampling for Early Prenatal Diagnosis of Cytogenetic Abnormalities," *The New England Journal of Medicine*, 320(10):609–617, Mar. 9, 1989.

Angie Rizzino, et al., "Defined Media and the Determination of Nutritional and Hormonal Requirements of Mammalian Cells in Culture," *Nutrition Reviews*, 37(12):369–378, Dec. 1979.

D. E. Rooney, et al., "Tissue Culture Methods in Human Cytogenetics," Chapter 1:1–37, *Human Cytogenetics: a practical approach*, 1989, Oxford IRL Press, Washington, D.C.

D. E. Rooney, et al., "Early amniocentesis: a cytogenetic evaluation," *British Medical Journal*, 298(6690);25, Jul. 1, 1989.

Carl V. Smith, "Amniotic Fluid Assessment," i Obstetrics and Gynecology Clinics of North America, 17(1):187–200. Mar. 1990.

Debra J. Wright, et al., "Interpretation of Chorionic Villus Sampling Laboratory Results is Just as Reliable as Amniocentesis," *Obstetrics & Gynecology*, 74(5):739–744, Nov. 1989.

Laird G. Jackson, et al. "A Randomized Comparison of Trancervical and Transabdominal Chorionic–Villus Sampling," *NE J. of Medicine*, 327:594–598, Aug. 1992.

Marco Londei, et al., "Interleukin 7 is a growth Factor for Mature Human T Cells," *Eur. J. Immunol.*, 20:425–428, 1990.

J. Mendelsohn, et al., "Proliferation of Normal Human Lymphocytes in Serum–free, Albumin–free Medium," in D. Sirbasku, et al., eds., *Proceedings of Cold Springs Harbor Conference on Cell Proliferation, Growth of Cells in Hormonally Defined Media*, 9:677–690, 1982.

M. B. Widmer, et al., "Lymphopoiesis and IL–7," *Int. J. of Cell Cloning*, 8:168–172, Supp. 1, 1990.

PRENATAL DIAGNOSIS BY CYTOKINE-INDUCED PROLIFERATION OF FETAL T-CELLS

FIELD OF THE INVENTION

The invention applies the technical field of cell biology to the development of novel methods of prenatal diagnosis.

BACKGROUND OF THE INVENTION

In certain disease states, the genetic component predominates over environmental factors. These diseases are termed genetic disorders and typically fall into one of three categories: (1) disorders characterized by the absence, excess, or abnormal arrangement of one or more chromosomes; (2) Mendelian or simply-inherited disorders, primarily caused by a single mutant gene and subclassified into autosomal dominant, autosomal recessive, or X-linked types; and (3) multifactorial disorders caused by interaction of multiple genes and environmental factors. The economic cost of genetic disorders is enormous. For example, the annual U.S. expenditure on treatment for the genetic disease cystic fibrosis alone is estimated at about $500 million. Cystic fibrosis and other genetic diseases account for the presence of at least one-third of the children in pediatric hospitals. Thompson & Thompson, *Genetics in Medicine* (4th ed. 1986). The psychological and emotional costs to those afflicted with genetic disorders and their families are incalculable.

Prenatal diagnosis and genetic counselling are important in detecting, preventing, and treating genetic disorders. If no abnormality is detected, parents' worries are diminished as the fetus is carried to term. If a fetal abnormality is detected sufficiently early, parents have the option of aborting the pregnancy. Occasionally, antenatal detection of an abnormality may allow its treatment before birth, or facilitate its treatment immediately after birth by notifying doctors when treatment is required and allowing for early preparation.

Techniques available for performing prenatal diagnosis include maternal serum screening, ultrasonography, chorionic villus sampling, fetal tissue screening, and amniocentesis. See, e.g., Kingston, *Brit. Med. J.* 298:1368–71 (1989); Platt & Carlson, *N. Engl. J. Med.* 327:636–638 (1992); *The Unborn Patient—Prenatal Diagnosis and Treatment* (Harrison, et al. eds., W. B. Sanders, Philadelphia, Pa. 1991) (each of which is hereby incorporated by reference in its entirety for all purposes). The techniques differ in their timing, safety, accuracy, rapidity, and scope of diagnostic markers they can detect. Early diagnosis is advantageous in facilitating therapeutic treatment, reducing the risk to the mother should an abortion be necessary, and in relieving parental anxiety should no problem be found.

Maternal serum screening involves virtually no risk to the fetus, but is useful only for detecting a few abnormalities such as neural tube defects. Ultrasonography also is safe, but can detect only structural characteristics, such as fetal size. Biochemical or genetic abnormalities cannot be detected using this method. Ultrasonography is typically used to determine fetal age and position in the womb in preparation of performing other diagnostic techniques. See, e.g., Hoybe in *The Unborn Patient—Prenatal Diagnosis and Treatment* (Harrison, et al. eds., W. B. Sanders, Philadelphia, Pa. 1991), ch. 8.

Chorionic villus sampling is a recently developed alternative to conventional amniocentesis. Chorionic villi are protrusions in the outermost extraembryonic membrane surrounding the fetus. In this method, chorionic villus tissue may be biopsied from 8 weeks gestation onward. Fibroblasts in the sample are cultured and subjected to biochemical or genetic testing. Typically 3–4 weeks are required to obtain a sufficient cell number to perform tests reliably. The early time at which chorionic villus sampling can be performed, as compared with conventional amniocentesis, is advantageous for the reasons discussed above. However, the increased risk of miscarriage or fetal deformation following chorionic villus sampling is four times greater than that following a conventional amniocentesis. See, Kingston, supra.

Fetoscopy involves obtaining tissue directly from the fetus and is performed during the second trimester of pregnancy. Cells can be cultured from the fetal tissue and subjected to biochemical and genetic tests. Fetoscopy involves five-fold higher risk to the fetus than amniocentesis. Thompson & Thompson, supra).

Embryo biopsy is possible at the 8–16 cell stage. See Handyside, *N. Engl. J. Med.* 327:905–9 (1992). One or two cells are scraped from the embryo, and subject to biochemical or genetic testing. Embryo biopsy is limited to those few pregnancies in which conception is by in vitro fertilization. In vitro fertilization is expensive to perform (see, e.g., *San Francisco Examiner* (Sep. 24, 1992)) and has a low probability of a successful pregnancy compared with conventional conception.

Amniocentesis (literally, tapping of the amnion) refers to a procedure of removing a sample of amniotic fluid transabdominally with a syringe. Conventionally, amniocentesis involves extraction of about 20 ml amniotic fluid from the amnionic sac at 14–16 weeks' gestation, when such volumes become available. Amniotic fluid contains mainly cells shed from the skin and digestive and urinary tracts of the fetus. Some diagnostic tests for proteins, such as α-fetoprotein, can be performed directly on the fluid. However, most tests require culturing cells within the fluid in order to provide sufficient cells or DNA for reliable analysis. In conventional amniocentesis, the cultured cells are fibroblasts and 3–4 weeks are required to achieve a sufficient cell number and density to perform diagnostic tests. Mandon & Mathieu, *J. Inher. Metab. Dis.* 12 suppl. 2:257–59 (1989). Extraction of the fluid causes an increased risk of miscarriage of about 0.5%. Thompson & Thompson, supra.

There have been several recent reports discussing amniocentesis performed earlier than the usual time of 14–16 weeks. In these reports, the volume of amniotic fluid extracted is generally smaller than in conventional amniocentesis, but the method of culturing cells in the fluid is the same. Elejalde, et al. report that amniocentesis is possible from the ninth week of pregnancy. *Am. J. Med. Gen.* 35:188–196 (1990). However, they found that early amniocentesis causes higher rates of fetal losses and amniotic fluid leakage. Elejalde, et al. also report that a longer time was required to obtain test data following early amniocentesis, because a smaller volume of fluid and, hence, fewer cells could be obtained and, therefore, longer culture periods were required.

Nevin, et al. also report that amniocentesis is possible from the ninth week of pregnancy. *Prenatal Diagnosis* 10:79–83 (1990). In this relatively small-scale experiment (222 patients), these authors found no increased risk of fetal loss compared with conventional amniocentesis. However, Nevin, et al. were able to extract only a much smaller volume of fluid (e.g., 4 ml for amniocentesis at 9 weeks) than the typical 20-ml volume extracted at 14-16 weeks.

Evans, et al. discuss early amniocentesis from 10-14 weeks of pregnancy. *Am. J. Obstet. Gynecol.* 160: 1332-9(1989). Evans, et al. report more frequent failure of cell cultures derived from early amniocentesis because of the difficulties associated with the smaller volume of fluid that could safely be extracted.

Holzgreve and Miny identify several problems when amniocentesis is performed earlier then 15 weeks. *Seminars in Perinatology* 13:260-277 (1988). These authors discuss the risks of withdrawing a greater proportion of total amniotic fluid than is the case for conventional amniocentesis performed at 14-16 weeks. These authors also discuss laceration of the extraembryonic celoma space or yolk sac and difficulties in interpreting a positive acetylcholinesterase test in early amniocentesis.

From the preceding discussion, it is apparent that withdrawing smaller volumes of amniotic fluid earlier in pregnancy and culturing cells by conventional methods is not an ideal means of performing prenatal diagnosis. Moreover, although alternative methods to amniocentesis are available, they lack the safety or general applicability of amniocentesis. Therefore, a need exists for improved methods of prenatal diagnosis that can be performed earlier in pregnancy and/or with greater safety, and/or rapidity, and/or accuracy than conventional amniocentesis. The present invention exploits a new method of culturing cells in amniotic fluid to fulfill this and other needs.

SUMMARY OF THE INVENTION

The present invention is based, in part, upon the observation that amniotic fluid contains T cells capable of proliferation, and discovery of means to proliferate such T cells, e.g., using cytokines and/or growth factors in a culture medium.

According to one embodiment of the invention, methods of prenatal diagnosis are provided. In some methods of prenatal diagnosis, a volume of amniotic fluid containing fetal cells is extracted from a pregnant woman. The fetal T-cells are propagated in a culture medium, e.g., comprising one or more cytokines and/or growth factors. The fetal T-cells are then used for diagnosis. The culture medium preferably contains cytokine IL-2, IL-4, or IL-7, and most preferably all three of these cytokines. The culture medium preferably also contains a feeder cell layer. Fetal T-cells are diagnosed by detecting a distinguishing cellular component such as a chromosome, nucleic acid, polypeptide, polysaccharide, or lipid. In a preferred embodiment, the distinguishing cellular component is one or more human leukocyte antigens which are detected by a direct cytotoxicity assay. The amniotic fluid is preferably extracted between about nine and sixteen weeks after conception, the volume of fluid extract is preferably between about one and five milliliters, and the fetal T-cells are preferably propagated for about seven to fourteen days before detecting a distinguishing cellular component.

In another embodiment, the invention provides a culture consisting essentially of fetal T-cells. The culture is produced by obtaining a volume of amniotic fluid from a pregnant woman and propagating the fetal T-cells present in the fluid in a culture medium comprising cytokines.

In another embodiment of the invention, a method of culturing fetal T-cells is provided. The fetal T-cells are obtained from a fetus and propagated in a culture medium comprising cytokines.

In another embodiment of the invention, a diagnostic kit is provided. The kit comprises compartments containing one or more cytokines, feeder cells, and/or reagents, e.g., for direct cytotoxicity or other assays of HLA antigens.

In another aspect of the invention, methods of treating a fetus are provided. In one method, fetal T-cells are obtained in amniotic fluid and propagated in a culture medium comprising one or more cytokines. The fetal T-cells are then used to diagnose a genetic defect, and if such a defect is found, it is corrected, e.g., by inserting a DNA segment containing a corrective gene into the fetal cells in utero or into the cord blood cells of both. In another method, fetal T-cells are obtained and propagated as in the previously described method. HLA antigens on the fetal T-cells are typed and compared with HLA antigens on potential donors to identify an appropriate donor. Hematopoietic stem cells are then transplanted from the donor to the fetus in utero.

In another aspect of the invention, a method of treating a person suffering from a disorder requiring bone marrow transplantation is provided. In this method, fetal T-cells are obtained in amniotic fluid, and propagated and HLA typed, as in the above methods. Cells from the person requiring transplantation are also HLA typed. The HLA antigens on the fetus and person are compared to determine immunocompatibility. If immunocompatibility is found, cord blood comprising hematopoietic stem cells is collected at the birth of the fetus. The stem cells are then transplanted into the person.

DESCRIPTION OF SPECIFIC EMBODIMENTS

I. General

According to one embodiment of the invention, improved methods of prenatal diagnosis are provided. The improvements are realized, in part, by the identification of a hitherto unknown component of amniotic fluid, namely T-cells of fetal origin, and the further discovery of novel culture conditions for propagation of fetal T-cells. By propagating fetal T-cells according to these methods it is possible to obtain sufficient cells to perform reliable diagnostic tests, within a shorter time, for the same volume of amniotic fluid, than is the case for conventional cell culture methods. This in turn means that earlier and/or safer and/or more rapid and/or more accurate prenatal diagnosis is possible than in conventional amniocentesis.

II. T-Cells

T-cells originate from lymphoid-committed stem cells of the fetus. Differentiation occurs principally in the second and third trimester of gestation, or immediately after birth. Therefore, early in pregnancy, the fetal population of T-cells largely comprises immature T-cells. Differentiation occurs in the thymus and proceeds through prothymocyte, cortical thymocyte, and medullary thymocyte intermediate stages, to produce various types of mature T-cells. Methods for culturing adult human T-cells in vitro have been described. See *Leukocyte Typing II,* Vol. 1 (Reinherz, et al. eds., Springer Verlag, N.Y. 1986) (which is hereby incorporated by reference in its entirety for all purposes).

III. Cytokines

Cytokine is a generic term for nonantibody soluble proteins which are released from one cell subpopulation and which act as intercellular mediators, for example, in the generation or regulation of an immune response. See *Human Cytokines: Handbook for Basic & Clinical Research* (Aggrawal, et al. eds., Blackwell Scientific, Boston, Mass. 1991) (which is hereby incorporated by reference in its entirety for all purposes). Cytokines include, e.g., interleukins IL-1 through IL-15, tumor necrosis factors α & β, interferons α, β, and γ, tumor growth factor Beta (TGF-β), colony stimulating factor (CSF) and granulocyte monocyte colony stimulating factor (GM-CSF). The action of each cytokine on its target cell, is mediated through binding to a cell surface receptor. Cytokines share many properties of hormones, but are distinct from classical hormones in that in vivo, they generally act locally on neighboring cells within a tissue. The activities of cytokines range from promoting cell growth (e.g., IL-2, IL-4, and IL-7), and arresting growth (IL-10, tumor necrosis factor and TGF-β), to inducing viral resistance (IFN α, β, and γ). See *Fundamental Immunology* (Paul ed., Raven Press, 2nd ed. 1989); *Encyclopedia of Immunology*, (Roitt ed., Academic Press 1992) (which are hereby incorporated by reference in their entirety for all purposes).

In one embodiment, the cytokine used to propagate fetal T-cells is IL-2,[1] IL-4, or IL-7. In another embodiment a combination of IL-2, IL-4, and IL-7 is used to propagate fetal T-cells. IL-2 is used at a concentration of about 0.1–1,000 Units/ml, preferably about 1–100 units/ml, more preferably about 5–20 Units/ml, and most preferably about 20 Units/mi. IL-4 is used at a concentration of about 1–10,000 Units/ml, preferably about 10–1,000 Units/ml, more preferably about 50–200 Units/ml, and most preferably about 200 Units/ml. IL-7 is used at a concentration of about 0.5–5,000 Units/ml, preferably about 5–500 units/ml, more preferably about 25–100 units/ml, and most preferably about 100 Units/ml. Some cytokines are less effective on cells from heterologous species. For example, mouse IL-3 and IL-4 are ineffective on human T-cells. It is therefore preferable that human cytokines be used.

Interleukins IL-2, IL-4 and IL-7 may be obtained from the supernatants of activated T-cells, from expression of cloned genes in mammalian or yeast cells, or from commercial sources. Growth factors known in the field of cell propagation may also be added. See, e.g., Rizzino, et al. (1979) *Nutritional Rev.* 37:369–378.

IV. Amniotic fluid

1. Extraction

Amniotic fluid is preferably withdrawn from the womb of a pregnant woman using, for example, a 20 or 22 gauge needle under continuous ultrasonic guidance. The volume of fluid to be extracted depends on the time during pregnancy, as discussed infra.

2. Composition

Amniotic fluid is composed largely of fetal urine and cells shed from the fetal skin, lung, and gastrointestinal tract. Smith, *Obstet. & Gynecol. Clinics N. America* 17:187–200 (1990) (which is hereby incorporated by reference in its entirety for all purposes). Example 2 identifies fetal T-cells as an additional component of amniotic fluid. Although only a minor component of natural amniotic fluid, fetal T-cells can be expanded to become the predominant component by culture conditions revealed by the present application.

3. Culturing Cells from Amniotic Fluid

The amniotic fluid is first centrifuged to separate amniotic cells from supernatant. The supernatant contains certain proteins diagnostic of fetal condition and can be subject to direct biochemical analyses. For example, high concentrations of α-fetoprotein or acetylcholinesterase are diagnostic of neural tube defects.

Conventional methods of culturing amniotic cells result in proliferation of the predominant cellular component of amniotic fluid, namely fibroblasts. For example, Mandon and Mathieu, supra, propagated amniotic fluid in HamF 10 medium supplemented with 10% fetal calf serum and 1% Ultroser G (IBF) supplemented with antibiotics. Conventional methods for culturing amniotic cells are also described by Rooney & Czepulkowski, *Human Cytogenetics: A Practical Approach* (Oxford Press 1986), pp. 1–36 (which is hereby incorporated by reference in its entirety for all purposes).

In the present methods, culture conditions are selected to ensure propagation of the small minority of T-cells in the amniotic fluid. This is achieved by supplementing a standard culture media (e.g., Yssel's medium, Yssel, *J. Immunol. Methods* 72:219 (1984) (which is hereby incorporated by reference in its entirety for all purposes), or RPM1-1640 medium plus fetal calf serum) with cytokines. Yssel's medium is a preferred starting medium because it is defined and allows reproducible results in growing similar cell types. Serum components can be replaced with various defined components capable of promoting growth of the desired cells. See, e.g., Iscove's medium components (GIBCO catalog); Barnes, et al. (1980) *Analytical Biochemistry* 102:255–270; Barnes, et al. (1980) *Cell* 22:649–655; Murakami, et al. (1982) *Proc. Nat'l Acad. Sci. USA* 79:1158–1162; and Leanderson (1985) *Immunological Methods* 3:201–208 (each of which is incorporated by reference in it its entirety for all purposes). Certain components, or their equivalents, are important supplements, e.g., transferrin, insulin, free fatty acids, ethanolamine, and carrier BSA. See also Sirbasku, et al. (eds.) (1982) *Proceedings of Cold Spring Harbor Conference on Cell Proliferation, Growth of Cells in Hormonally Defined Media*, vol. 9, particularly Mendelsohn, et al., pages 677–690. Human serum (e.g., type AB positive serum) can also be substituted for fetal calf serum. After an initial dose of cytokines, additional booster doses are preferably given every 3–6 days. Preferably, cytokines are added in such proportions and amounts as to stimulate the growth of T-cells, and a medium selected so as not to support the growth of fibroblasts. The propagation of fibroblasts is undesirable because fibroblasts may compete with, and impair the growth of, the fetal T-cells that are the subject of diagnosis.

In a preferred embodiment, the culture medium for propagation of fetal T-cells is supplemented with feeder cells, in addition to one or more cytokines and phytohemagglutinin (PHA). Suitable feeder cells include activated irradiated allogenic peripheral blood mononuclear and irradiated allogeneic Epstein Barr virus transformed B cells. The feeder cells provide a source of allogenic antigens and can provide useful supplementary cytokines to sustain T-cell proliferation. The feeder cells are usually added within twenty-four hours of commencing T-cell propagation. Booster dosages can also be added at 4–7 day intervals thereafter. Feeder cells generally disappear after 4–7 days. However, it is occasionally useful to remove feeder cells prior to analysis of T-cells by ficoll-hypaque gradient centrifugation.

V. Timing, Volume, and Risk

The time during pregnancy at which amniotic fluid is extracted, the volume of fluid extracted, the time required to culture cells, and the risk of the extraction to the fetus are interrelated. The earlier fluid is extracted during pregnancy, the smaller the volume that can be extracted for the same risk. The smaller the volume of fluid extracted, the longer the time required to culture cells. For many diagnostic tests, much of the time taken to obtain a result is spent culturing cells.

In conventional amniocentesis, about 20 ml fluid is extracted at 14–16 weeks, cells take 3–4 weeks to culture, and the risk to the fetus is about 5 miscarriages per 1000 amniocenteses. In early amniocentesis, performed using conventional fibroblast culturing methods, smaller volumes of fluid are extracted, typically 1 ml fluid per week of pregnancy, (see, e.g., Evans, et al., supra).

In the present methods, amniotic fluid is preferably extracted earlier than the conventional time of 14–16 weeks, most preferably from 9–14 weeks, but even earlier times such as 7 or 8 weeks are also possible. The volume of amniotic fluid is preferably considerably smaller than the volume of about 20 ml of fluid extracted at 14–16 weeks in conventional amniocentesis or the volume of 1 ml per week of pregnancy for early amniocentesis using conventional culturing methods. Successful diagnostic results can be obtained from as little as about 1–5 ml or less, of amniotic fluid. Notwithstanding the small size of the sample, cell cultures are preferably grown to sufficient density for assay after only about 7–10 days, although sometimes sufficient density can be obtained even earlier, such as after about 5 or 6 days. The shorter growth times compared with conventional amniocentesis are the result of two factors. First, T-cells propagated by the present methods grow more rapidly than fibroblasts propagated by conventional methods. Second, for some diagnostic techniques, particularly HLA typing, see, infra, the test can be performed on a smaller number of T-cells than fibroblasts, so cell growth may be terminated at a lower density.

VI. Uses

1. Diagnosis

A large number of abnormalities and diseases can be diagnosed from fetal T-cells propagated under the above-described growth conditions. These include Downs syndrome, muscular dystrophy, congenital malformation syndromes, hemophilia, and other X-linked diseases, Tay-Sachs disease, Lesch-Nyhan syndrome, cystic fibrosis, hematological disorders, such as thalassemia, aplastic anemia, leukemia, and Fanconi anemia, severe combined immuno-deficiency diseases, and metabolic disorders, such as Hunter's or Hurler's syndrome.

The diagnostic test usually requires the detection of a distinguishing cellular component. For example, some diseases and conditions can be diagnosed by detecting a distinguishing DNA sequence in the genomes of isolated fetal cells. DNA sequences can be analyzed by Southern blotting and/or the polymerase chain reaction. These methods either directly identify genetic loci associated with diseases and conditions or identify restriction fragment linked polymorphisms (RFLP) associated with genetic loci. Diseases and conditions detectable by these methods include, for example, thalassemias, hemoglobinopathies, Huntington disease (Gusella, *Nature* 306:234–238 (1983)) and hemophilia (Gianelli, *Lancet* 1:239–241 (1984)). See generally, Boehm & Kazazlan, "Prenatal Diagnosis by DNA analysis," in *The Unborn Patient* (Harrison, et al. eds., Saunders, PA, 2d ed. 1991), pp. 82–91 (each of which is hereby incorporated by reference in its entirety for all purposes).

Other diseases and conditions can be analyzed by isolating whole chromosomes. The chromosomes are banded and visualized under a microscope. Comparative analysis of the fetal banding pattern with those of the parents reveals whether the fetus has inherited a genetic defect from a parent. The method also detects gross chromosomal abnormalities. These abnormalities are more frequent in the fetuses of older women, and usually presage abnormal developments.

Other diseases and conditions can be diagnosed by analysis of fetal-cell proteins. Particularly for cell surface proteins, this analysis is conveniently effected by an immunological assay. Proteins can also be analyzed by protein sequencing, peptide mapping, electrophoresis, or by quantifying enzymic activity.

Other diseases and conditions are diagnosed by analysis of polysaccharides. Polysaccharides may be analyzed, e.g., by immunological tests or by gel electrophoresis.

Other diseases and conditions are diagnosed by analysis of fetal T-cell lipids. These may be broken down to their constituents by, for example, phospholipase digestion, and then subjected to chemical analyses, such as HPLC.

In a particularly preferred embodiment, the cellular component for diagnosis is a cell surface antigen. Human leukocyte antigens [HLA]are especially preferred. HLA antigens are encoded by the major histocompatibility complex, which has been localized to a specific region of the human chromosome 6p. The five known HLA loci are designated HLA-A, HLA-B, HLA-C, HLAD, and HLA-DR (D-related). Each loci has numerous alleles: at least 25 for HLA-A, over 40 for HLA-B, at least 10 for HLA-C, and at least 80 for HLA-D and HLA-DR. Klein, *Natural History of the Major Histocompatibility Complex* (Wiley, N.Y. 1986) (which is hereby incorporated by reference in its entirety for all purposes). The expression products of HLA-A, B, and C genes are referred to as Class I products and those of D and DR antigens are referred to as Class II products.

HLA typing is more easily performed on T-cells than on fibroblasts. Only $2-3 \times 10^6$ T-cells are required compared with $3-4 \times 10^7$ fibroblasts. Moreover, whereas only indirect cytotoxicity assays can be performed on fibroblasts, T-cells are also amenable to direct cytotoxicity assays. In a direct cytotoxicity test, HLA-specific antigen and complement are added to the lymphocytes under test, and the presence of HLA antigen on the lymphocytes is detected directly by cell lysis. See Stocker & Bernoco, in *Immunological Methods* (eds. Leftkovits & Pernis, Acad. Press 1979), pp. 217–226 (which is hereby incorporated by reference in its entirety for all purposes). In an indirect cytotoxicity test, HLA-specific antibody is added to cells under test (e.g., fibroblasts) without complement. Unound antibody is then washed off and mixed with a control lymphocytes in the presence of complement. Antibody not bound to the cells under test is therefore detected indirectly by lysis of control lymphocytes. See, e.g., Betuel, *Bone Marrow Transplantation* 9(1): 60–63 (1992) (which is hereby incorporated by reference in its entirety for all purposes). Direct cytotoxicity assays are more accurate and easier to perform than indirect assays.

Comparative analysis of fetal HLA patterns with those of parents and relatives is useful in a number of respects. The HLA antigens are directly diagnostic of immunocompatibility. The known availability of immunocompatible donors is valuable in performing bone marrow transplants in utero, as discussed infra. HLA patterns are also useful for determining the presence or absence of linked genetic loci responsible for genetic abnormalities. For example, the gene coding for 21-hydroxylase is located on chromosome 6 between HLA B and DR. See Forest, *Prenatal Diagnosis* 1:197–207 (1981). Mutations in this gene result in congenital adrenal hyperplasia. If it is found that fetal T-cells have the same variants of HLA B and DR as an affected sibling, it is concluded that the fetus is also affected. The presence of other genetic abnormalities linked to HLA antigens, such as polymorphisms in the enzyme glycoxylase and the congenital condition oligopontocerebellar ataxia, can be similarly identified.

2. Therapy

In some instances, early prenatal diagnosis facilitates treatment of an abnormality revealed by the diagnosis. See generally, Harrison, in *The Unborn Patient—Prenatal Diagnosis and Treatment* (Harrison, et al. eds., W. B. Sanders, Philadelphia, Pa.), ch. 17. For example, comparative HLA typing is used to identify appropriate (i.e., immunocompatible) hematopoietic stem cell donors. Immunocompatible donors are preferably HLA-identical siblings of the recipient. However, transplantation has also successfully been performed from unrelated donors who are identical at four HLA loci to the recipient. See Paul, supra. Stem cells from an appropriate donor are then transplanted, e.g., in utero, to a fetus suffering from hematological, metabolic or immunodeficiency disorders. Touraine, *Lancet* 1:1382 (1989); Touraine, *Bone Marrow Transpl.* 9(1): 121–126 (1992) (which are hereby incorporated by reference in their entirety for all purposes). Stem cells may also be transplanted within a few days of birth. Particular disorders susceptible to this treatment include thalassemia, aplastic anemia, Fanconi anemia, Hunter's or Hurler's syndrome, and combined immuno-deficiency diseases. Thomas, *J. Clin. Oncol.* 1: 517–531 (1983) (which is hereby incorporated by reference in its entirety for all purposes).

Early diagnosis is also advantageous for correction of fetal abnormalities by gene therapy. See Rosenberg, *J. Clin. Oncol.* 10:180–199 (1992); Cournoyer and Caskey, *Ann. Rev. Immunol.* 11:297–329 (1993). Gene therapy is more successful when performed in utero than after birth, because of the undifferentiated nature of cells in a developing fetus. Exogenously supplied corrective genes integrate into the genomes of undifferentiated cells, and are subsequently distributed and expressed in entire tissues by the proliferation and differentiation of the ancestor cell.

In other instances, earlier diagnosis is advantageous in facilitating preparation for treatment, e.g., after birth. For example, prenatal HLA typing is useful as a preliminary to performing corrective stem cell transplantation to a relative or other immunocompatible recipient of a fetus, soon after birth of the fetus. Broxmeyer, *Proc. Natl. Acad. Sci. USA* 86:3828–3832 (1989); Gluckman, *N. Engl. J. Med.* 321:1174–1178 (1989) (which are hereby incorporated by reference in their entirety for all purposes). Umbilical cord blood cells, which are a good source of hematopoietic stem cells, can be collected at the moment of birth and used for transplantation to the relative soon after birth.

VII. Other Embodiments

Amniotic fluid is not the only source of fetal T-cells for culture and diagnosis according to the present invention. In an alternative embodiment, fetal T-cells are obtained from other sources, for example, from fetal blood. Methods for obtaining fetal blood are described by Daffos in *The Unborn Patient—Prenatal Diagnosis and Treatment* (Harrison, et al. eds., W. B. Sanders, Philadelphia, Pa. 1991), ch. 11. T-cells in fetal blood are then cultured according to the same principles as T-cells contained in amniotic fluid.

In another aspect of the invention, a cell culture consisting essentially of fetal T-cells is provided. The culture is the result of propagating fetal T-cells from amniotic fluid in a culture medium containing cytokines. The cells are further characterized by fluorescent activated cell sorter analysis of the antigens expressed (see Example 1). The cell cultures are useful for performing prenatal diagnostic assays.

In another embodiment, the invention provides a method of culturing fetal T-cells according to the principles discussed in the prenatal diagnosis method. The method is useful for propagating a culture of fetal T-cells on which to perform prenatal diagnosis. The method is also useful for analyzing fetal T-cell differentiation and proliferation and identifying therapeutic agents affecting these processes.

The broad scope of this invention is best understood with reference to the following examples, which are not intended to limit the invention to the specific embodiments.

EXAMPLES

Example 1

Identification of Fetal T-Cells in Cytokine-Cultured Amniotic Fluid

About 1–5 ml of amniotic fluid was extracted from pregnant women at the fourteenth to sixteenth week of gestation. The fluid was placed in a 15 ml sterile tube and centrifuged for about 5 minutes at about 1000 rpm at room temperature. The pellet was resuspended in about 1 ml of Yssel's medium (Yssel, J. *Immunol. Methods* 72:219–225 (1984)) containing about 20 U/ml of IL-2 (Smith, *Science* 240:1169–1176 (1988)), about 200 U/ml of IL-4 (Spits, *J. Immunol.* 139:1142–1145 (1982)), and about 100 U/ml of IL-7 (Welch, *J. Immunol.* 143:3562 (1989)), in 24-well Linbro plates (each cited publication is hereby incorporated by reference in its entirety for all purposes). After overnight incubation, 0.5 ml of medium was removed and 0.5 ml of feeder cell mixture was added. The feeder cell mixture consisted of about $10^6$/ml PBMC from a normal donor, about $10^5$ cells/ml from the Epstein Barr virus transformed B cell line, JY EBV-LCL, and about 0.1 $\mu$g/ml of phytohaemagglutinin (PHA) (Roncarolo, *J. Exp. Med.* 167:1523–1530 (1988)). The PBMC were isolated from freshly obtained peripheral blood by centrifugation over hypaque. The PBMC were irradiated with 4000 rads, spun for 10 min at 1400 rpm in a standard table top centrifuge and resuspended in Yssel's medium at a concentration of $1$–$2\times10^6$ cells/ml. The JY EBV-LCL cells were irradiated with 5000 rads, spun down and resuspended in Yssel's medium at a concentration of $1$–$2\times10^5$ cells/ml.

After about 5-6 days, about 0.5 ml of medium containing IL-2, IL-4, and IL-7, at the previous concentrations, was added to the culture of amniotic cells. When cell density reached about $2 \times 10^6$ cells/ml, the cultures were split into two. Each cell culture was counted every six or seven days, and restimulated with the feeder cell mixture supplemented with IL-2, IL-4, and IL-7 at the previous concentration. Viable cells were counted every other day by Trypan blue exclusion. HLA typing was performed by a standard cytotoxic assay (Betuel, Human Immunol. 8:227-230 (1983)).

The number of cells expanded under these in vitro culture conditions is shown in Table 1. FACS analysis of the cells on day 18 showed that about 94% of the cells were CD2+, about 71% of the cells expressed CD3+, about 23% expressed the $\alpha\beta$TcR (BMA31 mAb) and 49% expressed the $\gamma\partial$ TcR, about 22% were CD4+, about 7% were CD8+. These results demonstrate that the cells expanded in vitro are T cells. The $\gamma\partial$ TcR T cells were positive for BB3 and Tigy mAbs which recognize V$\partial$2, indicating that these cells use the V$\partial$2 V$\gamma$9 and are comparable in their rearrangement patterns to the majority of $\gamma\partial$ TcRT cells present in adult peripheral blood and to $\gamma\partial$ TcR+T cells present in the fetal thymus (Spits, *Seminars in Immunol.* 2:119-130 (1991)) (hereby incorporated by reference in its entirety for all purposes).

TABLE 1

| Experiment Number | Volume (ml) | Number of cells ($10^{-3}$ — x ml) | | | |
|---|---|---|---|---|---|
| | | day 0 | day 7 | day 14 | day 18 |
| 1 (JW) | 5 | <10 | 400 | 2,500 | 10,000 |
| 2 (JZ) | 1 | <10 | 200 | 2,900 | ND |
| 3 (BD) | 1.5 | <10 | 2,400 | 40,000 | ND |
| 4 (GB) | 1 | <10 | 200 | 1,600 | ND |

Example 2

Prenatal Diagnosis of Expanded Fetal T-Cells

The HLA typing of a fetus was performed on cells after 20 days of culture. The results were compared to those obtained by HLA typing of peripheral blood mononuclear cells (PBMCs) from the parents and from the cord blood at the moment of birth. As shown in Table 2, the HLA phenotype of the amniotic cells is identical to that of the cord PBMCs, demonstrating that the cells expanded in vitro are of fetal origin.

TABLE 2

| | HPLA Typing | | | | |
|---|---|---|---|---|---|
| | A | B | C | DR | DQ |
| In vitro cultured amniotic T cells | 1, 30 | 18, 51 | | 3, X | 2, 7 |
| Cord blood | 1, 30 | 18, 51 | 5 | 3, 13 | 2, 7 |
| Mother | 1, X | 8, 51 | 5 | 3, 13 | 2, 7 |
| Father | 2, 30 | 18, 62 | 3 | 4, 3 | 2, 3 |

X indicates homozygous or undetermined marker

Example 3

Titration of Cytokines in Growth Medium

Amniotic fluid is extracted as described in Example 1. Preferably a large amount is combined to accumulate enough cells to test various concentrations of each growth factor. Titration is performed with each of the designated growth factors, over a ranges of at least 100-fold variation in concentration. For IL-2, IL-4, and IL-7, the concentrations used in Example 1 are useful starting points for titration. Depending upon conditions, the titrations are performed independently for each factor while the concentrations of other factors are held constant. Titrations of IL-2, IL-4, and IL-7 are performed, along with other factors such as transferrin, insulin, free fatty acids, ethanolamine, and BSA. Growth of the fetal T cells is assayed as described in Example 1 or from other biochemical, genetic, or histological markers.

Although the foregoing invention has been described in some detail by way of illustration and example, for purposes of clarity of understanding, it will be obvious that certain changes and modifications may be practiced within the scope of the appended claims.

All publications, patents, and patent applications cited above are hereby incorporated by reference in their entirety for all purposes to the same extent as if each were individually denoted as being incorporated by reference.

What is claimed is:

1. A method of prenatal diagnosis comprising:
   a) obtaining a volume of amniotic fluid containing fetal T-cells;
   b) propagating said fetal T-cells in a culture medium comprising one or more cytokines; and
   c) diagnosing said fetal T-cells.

2. The method of claim 1, wherein:
   said amniotic fluid further comprises fetal fibroblasts; and in said propagating step, said fetal T-cells replicate more rapidly than said fetal fibroblasts.

3. The method of claim 1, wherein said cytokines comprise interleukins IL-2, IL-4, or IL-7.

4. The method of claim 1, wherein said cytokines comprise interleukins IL-2, IL-4, and IL-7.

5. The method of claim 4, wherein said cytokines are:
   (a) IL-2 at a level of at least about 10 Units/ml;
   (b) IL-4 at a level of at least about 100 Units/ml; and
   (c) IL-7 at a level of at least about 50 Units/ml.

6. The method of claim 5, wherein said interleukins are human interleukins.

7. The method of claim 6, wherein a feeder cell mixture is added to said medium.

8. The method of claim 7, wherein said diagnosis is detecting a distinguishing cellular component.

9. The method of claim 8, wherein said distinguishing cellular component is a chromosome, nucleic acid, polypeptide, polysaccharide, or lipid.

10. The method of claim 9, wherein said distinguishing cellular component is diagnostic for a hematological, metabolic, or immunodeficiency disease.

11. The method of claim 9, wherein said diagnosis is a direct cytotoxicity assay and said distinguishing cellular component is one or more human leukocyte antigens on said fetal T-cells.

12. The method of claim 11, wherein said one or more HLAs comprise an HLA class I antigen or an HLA class II antigen.

13. The method of claim 12, wherein said assay for said HLA class I antigen is simultaneous with said assay for said HLA class II antigen.

14. The method of claim 13, wherein said volume of amniotic fluid is obtained between fourteen and sixteen weeks after conception.

15. The method of claim 14, wherein said volume is between one and five milliliters.

16. The method of claim 15, wherein said fetal T-cells are propagated for about seven to fourteen days.

* * * * *